(12) United States Patent
Weinstein

(10) Patent No.: US 6,270,796 B1
(45) Date of Patent: *Aug. 7, 2001

(54) ANTIHISTAMINE/DECONGESTANT REGIMENS FOR TREATING RHINITIS

(76) Inventor: Robert E. Weinstein, 177 Commonwealth Ave., Boston, MA (US) 02116

(*) Notice: Subject to any disclaimer, the term of this patent is extended or adjusted under 35 U.S.C. 154(b) by 0 days.

This patent is subject to a terminal disclaimer.

(21) Appl. No.: 09/182,297

(22) Filed: Oct. 29, 1998

Related U.S. Application Data

(60) Provisional application No. 60/063,710, filed on Oct. 29, 1997.

(51) Int. Cl.[7] .............................. A61K 9/22; A61K 9/52; A61M 9/22; A61M 31/00
(52) U.S. Cl. .................. 424/457; 424/468; 604/890.1; 604/50; 604/54
(58) Field of Search ................... 424/457, 468; 604/890.1, 50, 54

(56) References Cited

U.S. PATENT DOCUMENTS

| | | | |
|---|---|---|---|
| 4,295,567 | * 10/1981 | Kundsen | 206/534 |
| 4,915,952 | 4/1990 | Ayer et al. | |
| 5,422,097 | * 6/1995 | Gwaltney | 424/45 |
| 5,807,579 | * 9/1998 | Vilkov et al. | 424/469 |
| 5,848,976 | * 12/1998 | Weinstein | 600/556 |

OTHER PUBLICATIONS

Chem. abstr., vol. 120, 1993 (Columbus, OH, USA), the abstract No. 370, Howarth, P.H. et al., "The Influence of Terfenadine and Pseudo–Ephedrine Alone and In Combination On Allergen–Induced Rhinitis." Int. Arch Allergy Immunol. 1993, 101(3), 318–21.

Chem. abstr., vol. 124, 1995 (Columbus, OH, USA), the abstract No. 45070, Bronsky, E. et al., "Comparative Efficacy and Safety of a Once–Daily Loratadine–Pseudoephedrine Combination Versus Its Components Alone and Placebo in the Management of Seasonal Allergic Rhinitis." J. Allergy Clin. Immunol. 1995, 96(2), 139–47.

Chem. abstr., vol. 113, 1990 (Columbus, OH, USA), the abstract No. 70445, Meltzer, E.O. "Antihistamine and Decongestant–Induced Performance Decrements." J. Occup. Med. 1990, 32(4), 327–34.

Chem. abstr., vol. 125, 1996 (Columbus, OH, USA), the abstract No. 75693, Williams, B.O. et al., "Efficacy of Acrivastie Plus Pseudoephedrine for Symptomatic Relief of Seasonal Allergic Rhinitis Due to Mountain Cedar." Ann. Allergy, Asthma, Immunol. 1996, 76(5), 432–38.

Chem. abstr., vol. 102, 1984 (Columbus, OH, USA) the abstract No. 17558, Cairns, M.J. et al., "The Effects of Phenylpropanolamine and Other Sympathomimetics on Food Consumption and Motor Activity in Mice." J. Pharm. Pharmacol. 1984, 36(10), 704–6.

\* cited by examiner

Primary Examiner—Russell Travers
(74) Attorney, Agent, or Firm—Bickel & Brewer

(57) ABSTRACT

A prefilled, unifying dispensing container of at least two different medication dosage units comprising a regimen for the treatment of rhinitis, indicia for distinguishing the dosage units, and coordinating instructions. The medications may be contained in bottles, blister packages, or pouches. Medications include antihistamine and nasal decongestant. One dosage is for administration when sedation is not desired and the other is for administration when stimulation is not desired.

18 Claims, 2 Drawing Sheets

ANTIHISTAMINE/DECONGESTANT REGIMENS FOR TREATING RHINITIS

RELATED APPLICATIONS

The applicants wishes to claim the benefit of U.S. Provisional Patent Application No. 60/063,710, dated Oct. 29, 1997, for REGIMEN FOR TREATING RHINITIS in the names of Robert E. Weinstein and Allan M. Weinstein.

BACKGROUND OF THE INVENTION

1. Field of the Invention

The present invention relates to rhinitis treatment regimens, more particularly, to prepackaged therapeutic regimens for the symptomatic treatment of rhinitis which combine decongestant and antihistamine medications in a manner so as to avoid sedation when sedation is undesired and to avoid stimulation when stimulation is undesired.

2. The Prior Art

Rhinitis refers to an inflammatory disorder of the nasal passages. The symptoms of rhinitis typically consist of sneezing, rhinorrhea, nasal congestion, and increased nasal secretions. Failure of treatment of rhinitis may lead to other disorders including infection of the sinuses, ears and lower respiratory tract.

Two types of oral medication are commonly used to treat rhinitis: decongestants and antihistamines. Decongestants and antihistamines differ in mechanism of action, therapeutic effects, and side effects. It is common practice to combine the use of these two to bring about more complete symptom relief of rhinitis than with either entity alone.

Decongestants commonly used to treat rhinitis include the adrenaline-like agents pseudoephedrine and phenylpropanolamine. These agents act to constrict vessels in the nasal mucus membranes and thereby decrease tissue swelling and nasal congestion. Decongestants are found to be better than antihistamines for restoring the patency of congested nasal airways. Like adrenaline, nasal decongestants are stimulatory and produce side effects which may be tolerated during the day, and even be considered desirable to counter fatigue which is known to accompany other symptoms of rhinitis. Decongestants, however, may produce nervousness, restlessness, and insomnia if taken at night. This can be a source of confusion for individuals who mistakenly attribute their inability to sleep to the malaise accompanying rhinitis rather than to the decongestant medication.

Histamine is a mediator released from cells which line the walls of the nasal mucous membranes (mast cells). When released, histamine is known to bind to local receptors and thereby cause sneezing, nasal itching, swelling of the nasal membranes, and increased nasal secretions. Antihistamines relieve these effects, albeit by a different mechanism than decongestants. Antihistamines block the binding of histamine to histamine receptors in the nasal membranes. Antihistamines preemptively bind to histamine receptors and are effective only if given prior to histamine release (once histamine is released and binds to the receptor, it is too late). Although individuals typically take antihistamines after symptoms occur, it is more desirable to dose antihistamine so as to effect therapeutic activity in anticipation of the peak times of histamine release. Individuals with rhinitis commonly experience peak symptoms in the morning hours on awakening, a time concomitant with peak histamine release and coinciding with peak exposure to airborne allergens which stimulate histamine release in sensitive individuals.

To improve upon the sedation of such older antihistamines, newer antihistamines with little or no sedation have more recently been developed.

The combining of decongestants and antihistamines utilizes two mechanistic approaches, and has been shown to offer more complete relief of rhinitis symptoms than therapy with either component alone. Consequently, many products have been formulated so that their dosage units contain both. While individuals are known to vary in their susceptibility to side effects, the incorporation of decongestant and sedating antihistamine into a single dosage unit represents an attempt to balance stimulation and sedation of the components. Consequently, some individuals experience irritability and/or sedation with these combinations. Examples of commercial formulations containing decongestant and sedating antihistamine include:

1. CHLOR-TRIMETON® 4 hour Allergy/Decongestant which contains 4 mg of chlorpheniramine (sedating antihistamine) and 60 mg pseudoephedrine sulfate (stimulating decongestant), and which is recommended to be taken every 4 to 6 hours (½ this dosage for children 6 to under 12);

2. CHLOR-TRIMETON® 12 hour Allergy/Decongestant which contains 8 mg of chlorpheniramine (sedating antihistamine) and 120 mg pseudoephedrine sulfate (stimulating decongestant), and which is recommended to be taken every 12 hours (adults and children over 12 years of age only);

3. BROMFED® Tablets which contains 4 mg of brompheniramine (sedating antihistamine) and 60 mg pseudoephedrine sulfate (stimulating decongestant), and which is recommended to be taken every 4 to 6 hours (½ this dosage for children 6 to under 12);

4. BROMFED® Capsules which contains 12 mg of brompheniramine (sedating antihistamine) and 120 mg pseudoephedrine sulfate (stimulating decongestant), and which is recommended to be taken every 12 hours (adults and children over 12 years of age only);

5. BENADRYL® Allergy Decongestant Tablets which contains 25 mg of diphenhydramine hydrochloride (sedating antihistamine) and 60 mg pseudoephedrine sulfate (stimulating decongestant), and which is recommended to be taken by adults and children over 12 years of age every 4 to 6 hours, not to exceed 4 tablets in 24 hours; and 6. TAVIST-D® Tablets which contains 1.34 mg clemastine fumarate (sedating antihistamine) and 75 mg phenylpropanolamine hydrochloride (stimulating decongestant), and which is recommended to be taken every 12 hours (adults and children over 12 years of age only).

More recently, formulations have been commercialized which incorporate both a decongestant and a non-sedating antihistamine into a single dosage unit. While such formulations offer the advantage in being non-sedating, such combinations might be expected to provoke a greater incidence of nighttime irritability and insomnia because the stimulating side effects of the decongestant are not attenuated by concomitant use of sedating antihistamine. Indeed, a 25% incidence of insomnia has been disclosed among users of the combination of non-sedating antihistamine terfenadine and pseudoephedrine. Examples of such formulations include:

1. SELDANE-D® Extended-Release Tablets which contains 60 mg terfenadine (non-sedating antihistamine) and 120 mg pseudoephedrine hydrochloride (stimulating decongestant), and which is recommended to be taken every 12 hours (adults and children over 12 years of age);

2. CLARITIN-D® 24 HOUR Extended-Release Tablets which contains 10 mg loratidine (antihistamine) and 240 mg pseudoephedrine hydrochloride (decongestant) and, which is recommended to be taken every 24 hours (adults and children over 12 years of age); and 3. ALLEGRA-D™ which contains 60 mg fexofenadine (non-sedating antihistamine) and 120 mg pseudoephedrine hydrochloride (stimulating decongestant), and which is recommended to be taken every 12 hours (adults and children over 12 years of age).

U.S. Pat. No. 4,295,567, issued to Knudsen, teaches a regimen to avoid sedation from antihistamines when sedation is undesired. The Knudsen patent therefore does not apply to antihistamines which are not sedating. In accordance with Knudsen, prepackaged regimens for treating the symptoms of rhinitis have been commercialized, and employ decongestant for daytime and decongestant plus sedating antihistamine for night. Examples in accordance with Knudsen include:

1. DAYTIME & NIGHTTIME ACTIFED ALLERGY® which contains 30 mg pseudoephedrine (decongestant) in the daytime formulation, and 30 mg pseudoephedrine (decongestant) and 25 mg diphenhydramine (antihistamine) in the nighttime formulation; and 2. CONTAC DAY & NIGHT ALLERGY/SINUS® which contains 60 mg pseudoephedrine (decongestant) and 650 mg acetaminophen (analgesic) in the daytime formulation, and 60 mg pseudoephedrine (decongestant), 50 mg diphenhydramine (antihistamine), and 650 mg acetaminophen (analgesic) in the nighttime formulation.

Regimens have also been commercialized which incorporate a decongestant for daytime and not for nighttime. An example of one such prepackaged regimen is SYN-RX™, which contains 60 mg pseudoephedrine HCL and 600 mg Guaifenesin in the day formulation, and 600 mg Guaifenesin in the nighttime formulation. These regimens avoid stimulation from decongestant at night, however lack antihistamine. Further, they neither contain medication which would be effective for rhinitis symptoms at night, nor anticipate peak symptoms of rhinitis in the morning hours on awakening.

While the problem of sedation with combined decongestant and sedating antihistamine treatment is addressed by Knudsen, the problem of nighttime irritability and insomnia is not. Indeed, all commercialized decongestant and antihistamine regimens according to Knudsen have the potential to cause irritability and insomnia at night.

Similarly, while the problem of sedation with combined decongestant and sedating antihistamine treatment are addressed in single entity combinations which employ decongestants and non-sedating antihistamines, the problem of nighttime irritability and insomnia is not. Formulations which incorporate decongestant and non-sedating antihistamine into a single dosage unit are yet more likely to produce irritability and insomnia at night than formulations with sedating antihistamine.

It is well known that individuals with rhinitis utilize antihistamines and decongestants hundreds of millions of times a year. It is not uncommon for inappropriate choices to result in symptomatic worsening rather than improvement. Individuals often use sedating medication unknowingly or inappropriately. Decongestants taken at night not only produce insomnia in a sizable portion of users, but also daytime irritability, fatigue, and malaise from lack of rest. Users are known to mistakenly ascribe such symptoms to rhinitis rather than to medication. Professional as well as consumer confusion is widely encountered with these medications and unnecessarily negative consequences occur both by self-selection and prescription. There is a present need for preformulated regimens which advantageously use antihistamines and decongestants for rhinitis in a manner to circumvent this confusion, and to avoid both daytime sedation and nighttime stimulation.

Adherence to medication therapy and prevention of medication error are considerable medical problems and are improved with measures to establish simplicity, reduce confusion, and increase convenience. The proposed use of a multiplicity of dosage units as a regimen may be associated with dosage units being confused with each other, inadvertently switched, lost, misplaced, or ignored. Another problem associated with treatment using a plurality of dosage units is the lack of indicia which distinguish the dosage units from each other and signify and verify their use together and readily available instructions for coordinating the medications. Individuals are known to lose instructions issued separate from the medication. Haphazard selection and organization of medications can result in treatment failure and in the patient's requiring additional medical attention involving time, expense, and personnel costs and effort to instruct and organize therapy. Cost factors and outcomes are being carefully considered in the current medical climate. Improvements in organization and teaching including devices and methods which would help patients be more cognizant of their proper therapeutic requirements are considered desirable in view of limitations in time and costs for medical personnel. Successful therapy for rhinitis is less costly than unsuccessful treatment which eventuates in complications or multiple clinic visits.

SUMMARY OF THE INVENTION

It is therefore an object of the present invention to utilize decongestants and antihistamines in formulations so as to provide regimens for the treatment of rhinitis that avoid sedation during the day and that also avoid stimulation at night. The terms "day" and "night" are intended to be synonymous with times when sedation is considered undesirable, such as when awake, and with times when stimulation is considered undesirable, such as bedtime, respectively, as well as literally daytime and nighttime, in that such times vary in accordance with the schedule of the individual.

It is another object to reduce confusion in the use of antihistamines and decongestants for the treatment of rhinitis.

The devising of such formulations and instructions for the use of such formulations requires pharmaceutical expertise and requires understanding of the actions, side effects, and pharmacokinetics of antihistamines, decongestants, and other formulated components, including components which effect the bioavailability of the active ingredients, as well as determination of the suitability of the components' use together. It is therefore another object of the present invention to provide a user with an expertly devised regimen.

It is a further object to provide a method and device for organizing, storing, and coordinating regimens for the treatment of rhinitis for the purpose of convenience in using such regimens by providing such regimens in a prepackaged container which incorporates coordinating indicia and instructions.

It is a further object to provide regimens which provide dosing of antihistamine in accordance with its kinetics so as to achieve histamine receptor binding in the morning hours, at the conventional time of awakening, which such scheduling is desired.

It is a preferred object to provide a user with an therapeutic combination of decongestant and antihistamine during the day, either by single nighttime dosing of sedating antihistamine which is suitable with respect to its half-life, duration of action, and duration of side effect, or by utilization of non-sedating antihistamine.

The present invention provides for a prefilled, unifying dispensing container containing at least two modules of different dosage units for the treatment of rhinitis, indicia for distinguishing the dosage units and signifying their use together, and coordinating instructions for their use. The container can have one of any number of forms, including, but not limited to, a box with the dosages in bottles, a blister package, a box of individual blister packages, or a box of pouches.

There are at least two different dosages combining to form a regimen for the treatment of rhinitis. The dosages are combinations of medications that include antihistamine and nasal decongestant. One dosage is for administration when sedation is not desired and the other is for administration when stimulation is not desired. There are a number of possible combinations of decongestants and antihistamines presently available that can be employed in the present invention. Other medications, such as analgesics, may be incorporated into the dosages.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Figure 1:
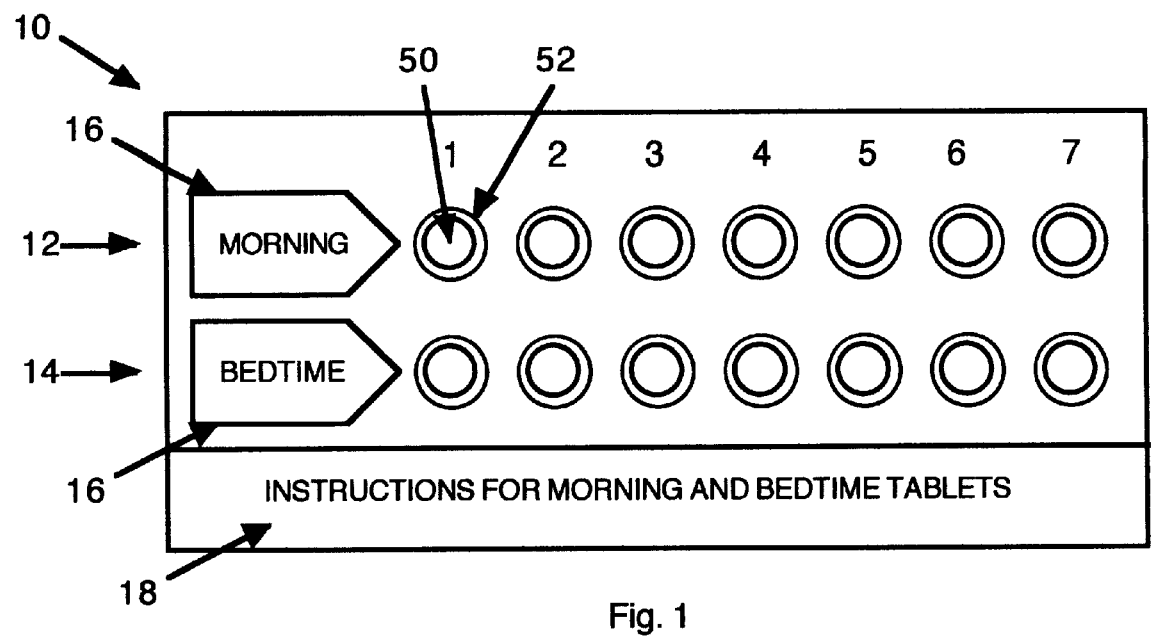
FIG. 1 is a plan view of one embodiment of the present invention.

The present invention provides for a prefilled, unifying dispensing container containing at least two modules of different dosage units for the treatment of rhinitis, indicia for distinguishing the dosage units and signifying their use together, and coordinating instructions for their use. It is to be understood that either single or multiple modules of each dosage unit are contained. The dosage units may be in the form of tablet, pill, capsule, caplet, powders, liquids, gels, some of which may require reconstituting, or any generally recognized oral form of medication.

Referring to the drawings, it will be understood that while preferred embodiments of the invention have been illustrated and described, the invention is not limited to such embodiments. Changes and additions may be made therein and thereto without departing from the spirit of the invention.

Figure 2:
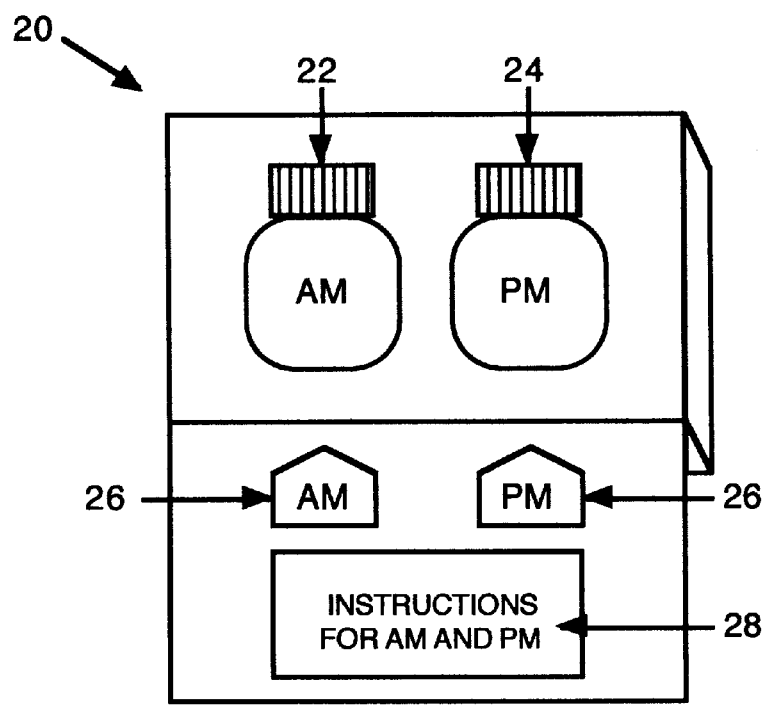
FIG. 2 is a top view of another embodiment of the present invention.
Figure 3:
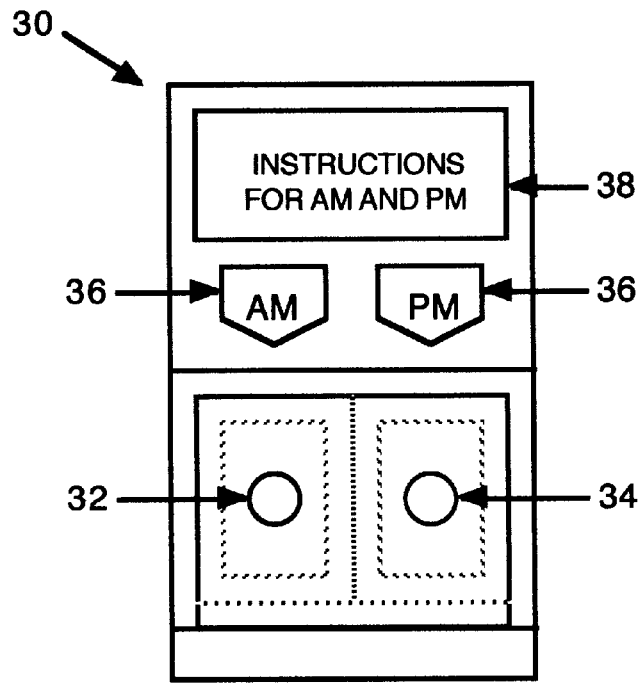
FIG. 3 is a plan view of a third embodiment of the present invention.
Figure 4:
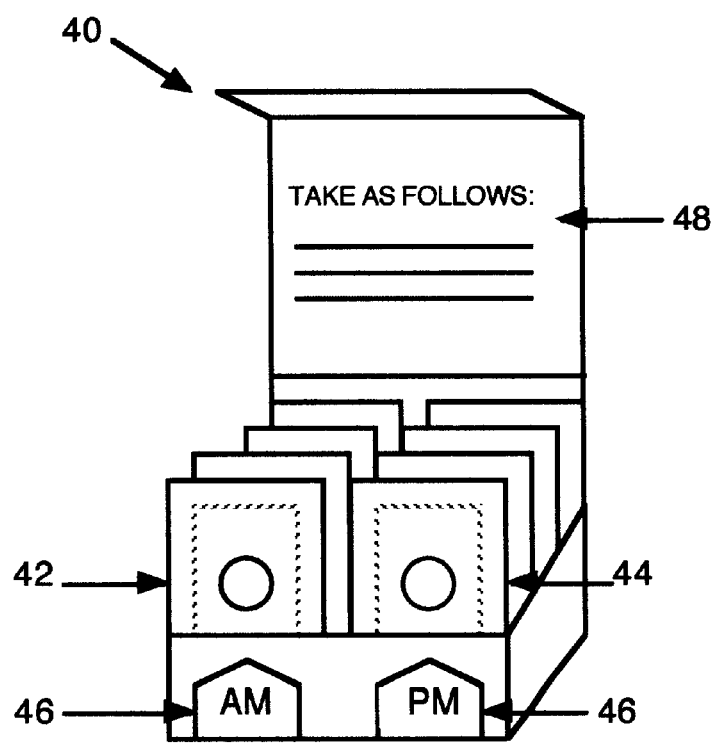
FIG. 4 is a front view of a fourth embodiment of the present invention.

Embodiments of the unifying container are depicted in FIGS. 1–4. FIG. 1 depicts a support package 10 containing multiple dosages of two different dosage units 12, 14 in tablet form 50 in blister packaging 52. FIG. 2 depicts a support package 20 which houses two modules in the form of bottles 22, 24 containing different dosage units, which can be in either liquid form or solid form. FIG. 3 depicts a support package 30 with a single dosage unit 32 for morning and a single different dosage unit 34 for night. FIG. 4 depicts a support package 40 which is manufactured to house a multiplicity of daytime modules in the form of pouches 42 and a multiplicity of nighttime modules in the form of pouches 44. In each of the four depicted configurations, the support package has specific provision for supporting the dosage units in physical accord with indicia 16, 26, 36, 46. The indicia manufactured with the support package distinguishes between the dosage units by means of wording, color, shape symbol, or other means known in the art. The indicia, by its presence, also indicates the suitability of the dosage units for use with each other. The support package incorporates coordinated administration instructions 18, 28, 38, 48 which also indicate the suitability of the dosage units for use with each other, and instruct coordination of the dosage units as a regimen.

Although the embodiments specifically described herein have two dosage modules, packaging containing other numbers of modules are also within the scope of this invention. The packaging may be adapted by widening the packaging and increasing the number of modules and indicia. Additionally, the packaging may be in any geometric configuration.

The packaging contains combinations of medications, which include nasal decongestants and antihistamines, that comprise a regimen for treating rhinitis. Specifically, the packaged medication is comprised of at least two dosage units, one for administration when sedation is not desired, as, for example, during the day, and one for administration when stimulation is not desired, as, for example, at night. The non-sedating dosage unit may be formulated to contain non-sedating antihistamine and/or decongestant, but not sedating antihistamine. The non-stimulating dosage unit may be formulated to contain sedating or non-sedating antihistamine, but not stimulating nasal decongestant. The regimen is devised utilizing a combination of dosage units which are favorable for use with each other, particularly with regard to pharmacokinetic and therapeutic characteristics. It is possible to formulate these regimens with presently available dosage units as well as with newly formulated dosage units. Examples of regimens, some of which employ presently available dosage units, are described below.

EXAMPLE 1

120 mg pseudoephedrine hydrochloride (stimulating decongestant) and 5 mg loratidine (non-sedating antihistamine) to be taken in the morning, and 5 mg loratidine to be taken at bedtime. Limiting pseudoephedrine dosing to the day avoids stimulation and insomnia at night when stimulation is undesired. Use of the non-sedating antihistamine, loratidine avoids sedation during the day. Loratidine is known to have a long half-life, exerting an antihistamine effect 1 to 3 hours after dosing, reaching a maximum at 8 to 12 hours, and lasting in excess of 24 hours. An effective daytime combination of decongestant and antihistamine would result from the dosing of both decongestant and non-sedating antihistamine in the morning.

EXAMPLE 2

120 mg pseudoephedrine hydrochloride (stimulating decongestant) to be taken in the morning and 10 mg loratidine (non-sedating antihistamine) to be taken at bedtime. In this instance, loratidine is dosed at bedtime and reaches a peak efficacy in the early morning hours, a time when symptoms typically peak. Although antihistamine is not dosed during the day, an effective daytime combination of decongestant and antihistamine results from the dosing of decongestant in the morning and loratidine at night because of the 24-hour duration of the antihistamine affect of loratidine.

EXAMPLE 3

120 mg pseudoephedrine sulfate (stimulating decongestant) and 60 mg of fexofenadine (non-sedating antihistamine) to be taken in the morning, and 60 mg of fexofenadine to be taken in the evening. Limitation of pseudoephedrine dosing to the day avoids stimulation and insomnia at night when stimulation is undesired. Use of the non-sedating antihistamine fexofenadine avoids daytime sedation. The 12-hour duration of fexofenadine requires a daytime dosing to achieve an effective daytime combination of antihistamine and decongestant. Bedtime dosing of fexofenadine anticipates early morning histamine release.

EXAMPLE 4

60 mg pseudoephedrine sulfate (stimulating decongestant) to be taken in the morning and afternoon, and 4 mg of chlorpheniramine (sedating antihistamine) to be taken at bedtime. Despite the traditional, and still current, indication for 4 to 6 hour dosing for chlorpheniramine, a single dose has more recently been is shown to inhibit the symptoms of rhinitis for more than 24 hours. Maximal sedation occurs approximately 3 to 4 hour after dosing and sedation persists not longer than 6 to 8 hours following dosing. Notably, the short duration of sedation in relation to the longer duration of symptom suppression favors dosing of chlorpheniramine at bedtime as a way to anticipate peak morning histamine release, and effectively confer combined antihistamine and decongestant activity during the day without sedation and without dosing of sedating antihistamine during the day. The limiting of pseudoephedrine dosing to day avoids the potential for stimulation and insomnia at night.

EXAMPLE 5

35 mg phenylpropanolamine (stimulating decongestant) to be taken in the morning and late afternoon, and 4 mg of chlorpheniramine (sedating antihistamine) to be taken at bedtime. This regimen is essentially the same as that of Example 4, substituting the decongestant phenylpropanolamine for pseudoephedrine.

In addition to antihistamines and decongestants, other therapeutic ingredients for the treatment of rhinitis may be formulated if desired. For example, analgesics such as salicylates and acetophenamin may be considered for inclusion in such formulations and are within the scope of the present invention.

These examples do not constitute an exhaustive list of potential combinations, and variations and modifications may be made by those of ordinary skill in the art.

Other variations may occur to those skilled in the art which are within the scope of the invention as set forth in the appended claims. Those of skill in the art may also recognize modifications to these presently disclosed embodiments. These variations and modifications are meant to be covered by the spirit and scope of the present claims.

What is claimed is:

1. A prepackaged therapeutic regimen comprising:
   (a) a non-sedating first dosage unit, which includes a nasal decongestant;
   (b) a second dosage unit which does not include a nasal decongestant and includes an antihistamine;
   (c) indicia for distinguishing between said first and second dosage units;
   (d) administration instructions for the use of said dosage units as a rhinitis regimen, such that said first dosage unit is instructed for daytime administration and said second dosage unit is instructed for nighttime administration; and
   (e) a pharmaceutical dispensing container prefilled with said dosage units and incorporating said indicia and instructions.

2. The prepackaged therapeutic regimen of claim 1 wherein said antihistamine is non-sedating.

3. The prepackaged therapeutic regimen of claim 1 wherein said antihistamine is sedating.

4. The prepackaged therapeutic regimen of claim 1 wherein said antihistamine is chlorpheniramine.

5. The prepackaged therapeutic regimen of claim 1 wherein said decongestant is pseudoephedrine.

6. The prepackaged therapeutic regimen of claim 1 wherein said decongestant is phenylpropanolamine.

7. The prepackaged therapeutic regimen of claim 1 wherein said dispensing container is a blister pack.

8. The prepackaged therapeutic regimen of claim 1 wherein said dispensing container incorporates bottles containing liquid medications.

9. The prepackaged therapeutic regimen of claim 1 wherein said dispensing container incorporates bottles containing solid medications.

10. A method for rhinitis treatment comprising the steps of:
    (a) formulating a rhinitis treatment regimen comprising a non-sedating first dosage unit which includes a nasal decongestant, and a second dosage unit which does not include a nasal decongestant and includes an antihistamine;
    (b) providing indicia for distinguishing between said first and second dosage units;
    (c) providing administration instructions for the use of said dosage units, such that said first dosage unit is instructed for daytime administration; and said second dosage unit is instructed for nighttime administration; and
    (d) prefilling a pharmaceutical dispensing container with said first and second dosage units and incorporating said indicia and instructions in said dispensing container for a user.

11. The method of claim 10 wherein said antihistamine is non-sedating.

12. The method of claim 10 wherein said antihistamine is sedating.

13. The method of claim 10 wherein said antihistamine is chlorphenlramine.

14. The method of claim 10 wherein said decongestant is pseudoephedrine.

15. The method of claim 10 wherein said decongestant is phenylpropanolamine.

16. The method of claim 10 wherein said dispensing container is a blister pack.

17. The method of claim 10 wherein said dispensing container incorporates bottles containing liquid medications.

18. The method of claim 10 wherein said dispensing container incorporates bottles containing solid medications.

* * * * *

(12) EX PARTE REEXAMINATION CERTIFICATE (9474th)
United States Patent
Weinstein

(10) Number: US 6,270,796 C1
(45) Certificate Issued: *Jan. 11, 2013

(54) ANTIHISTAMINE/DECONGESTANT REGIMENS FOR TREATING RHINITIS

(75) Inventor: Robert E. Weinstein, Boston, MA (US)

(73) Assignee: J-Med Pharmaceuticals, Inc., Boston, MA (US)

Reexamination Request:
No. 90/008,111, Jul. 7, 2006

Reexamination Certificate for:
Patent No.: 6,270,796
Issued: Aug. 7, 2001
Appl. No.: 09/182,297
Filed: Oct. 29, 1998

(*) Notice: This patent is subject to a terminal disclaimer.

Related U.S. Application Data

(60) Provisional application No. 60/063,710, filed on Oct. 29, 1997.

(51) Int. Cl.
*A61K 31/00* (2006.01)
*A61K 31/137* (2006.01)
*A61K 31/44* (2006.01)
*A61K 31/4402* (2006.01)

(52) U.S. Cl. .................... 424/457; 424/468; 604/890.1
(58) Field of Classification Search .................. None
See application file for complete search history.

(56) References Cited

To view the complete listing of prior art documents cited during the proceeding for Reexamination Control Number 90/008,111, please refer to the USPTO's public Patent Application Information Retrieval (PAIR) system under the Display References tab.

*Primary Examiner* — Sharon Turner

(57) ABSTRACT

A prefilled, unifying dispensing container of at least two different medication dosage units comprising a regimen for the treatment of rhinitis, indicia for distinguishing the dosage units, and coordinating instructions. The medications may be contained in bottles, blister packages, or pouches. Medications include antihistamine and nasal decongestant. One dosage is for administration when sedation is not desired and the other is for administration when stimulation is not desired.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-18 are cancelled.

* * * * *